United States Patent
Miller et al.

(10) Patent No.: US 11,627,955 B2
(45) Date of Patent: Apr. 18, 2023

(54) MULTI-DENSITY ALL SUTURE ANCHOR

(71) Applicant: Conmed Corporation, Utica, NY (US)

(72) Inventors: Peter Miller, Largo, FL (US); Thomas Kehoe, Tarpon Springs, FL (US)

(73) Assignee: Conmed Corporation, Utica, NY (US)

(*) Notice: Subject to any disclaimer, the term of this patent is extended or adjusted under 35 U.S.C. 154(b) by 255 days.

(21) Appl. No.: 16/771,975

(22) PCT Filed: Dec. 13, 2018

(86) PCT No.: PCT/US2018/065375
§ 371 (c)(1),
(2) Date: Jun. 11, 2020

(87) PCT Pub. No.: WO2019/118681
PCT Pub. Date: Jun. 20, 2019

(65) Prior Publication Data
US 2021/0068807 A1    Mar. 11, 2021

Related U.S. Application Data

(60) Provisional application No. 62/598,201, filed on Dec. 13, 2017.

(51) Int. Cl.
*A61B 17/04*  (2006.01)
(52) U.S. Cl.
CPC .. *A61B 17/0401* (2013.01); *A61B 2017/0409* (2013.01); *A61B 2017/0427* (2013.01); *A61B 2017/0496* (2013.01)
(58) Field of Classification Search
CPC ........ A61B 17/0401; A61B 2017/0406; A61B 2017/0409; A61B 2017/0464;
(Continued)

(56) References Cited

U.S. PATENT DOCUMENTS 5,256,762 A * 10/1993 Hermes ................... A61L 31/06
606/228
6,235,057 B1 * 5/2001 Roger .................... A61F 2/0811
623/13.12
(Continued)

FOREIGN PATENT DOCUMENTS

| JP | 2015-504314 A | 2/2015 |
| WO | 2016/154099 | 9/2016 |
| WO | 2017/136392 | 8/2017 |

OTHER PUBLICATIONS

JP Office Action, dated Jun. 24, 2021, Application No. 2020-531749, pp. 1-10.
(Continued)

*Primary Examiner* — Katherine M Shi
(74) *Attorney, Agent, or Firm* — Bond, Schoeneck & King, PLLC; Frederick J. M. Price

(57) ABSTRACT

An all-suture anchor for generating bone compression and increasing interference fixation. The all-suture anchor includes a fibrous construct which is movable between a pre-deployment configuration and a deployed configuration. The fibrous construct has a first density. The all-suture anchor also includes a monofilament woven through the fibrous construct. The monofilament has a second density, which is different than the first density. The contrasting densities (i.e., irregularities) aids in the "locking" ability of the all-suture anchor by greater purchase in hard and soft bone. The all-suture anchor can have a variety of textures, barbs, and rigidities that aid in creating irregularities within the bone surface for more secure fixation.

8 Claims, 7 Drawing Sheets

(58) Field of Classification Search
CPC ...... A61B 17/06166; A61B 2017/0496; A61B 2017/0427
See application file for complete search history.

(56) References Cited

U.S. PATENT DOCUMENTS

| | | | | |
|---|---|---|---|---|
| 9,198,656 | B1* | 12/2015 | Ferguson | ......... A61B 17/06166 |
| 9,826,971 | B2 | 11/2017 | Lombardo et al. | |
| 10,182,806 | B2 | 1/2019 | Foerster | |
| 2006/0052975 | A1* | 3/2006 | Krumm | ................... G01S 17/06 |
| | | | | 702/150 |
| 2007/0239275 | A1* | 10/2007 | Willobee | .................. A61F 2/08 |
| | | | | 623/13.17 |
| 2010/0222792 | A1* | 9/2010 | Barnes | ................. A61B 17/122 |
| | | | | 606/232 |
| 2012/0109196 | A1* | 5/2012 | McCaw | ............. A61B 17/0487 |
| | | | | 606/232 |
| 2015/0127049 | A1 | 5/2015 | Marchand | |
| 2016/0175088 | A1* | 6/2016 | Sengun | ..................... A61F 2/08 |
| | | | | 112/475.08 |
| 2016/0317162 | A1* | 11/2016 | Dougherty | ......... A61B 17/1633 |
| 2017/0055975 | A1* | 3/2017 | Thal | ................... A61B 17/0401 |
| 2017/0119369 | A1* | 5/2017 | Lombardo | ......... A61B 17/0401 |
| 2017/0128063 | A1* | 5/2017 | Jackson | ............. A61B 17/0401 |
| 2017/0273680 | A1 | 9/2017 | Sengun et al. | |
| 2017/0290578 | A1* | 10/2017 | Thal | ................... A61B 17/0401 |

OTHER PUBLICATIONS

International Search Report Form PCT/ISA/220, International Application No. PCT/US2018/65375, pp. 1-13, dated Mar. 27, 2019.
CA Office Action, dated Jun. 22, 2021, Application No. 3082842, pp. 1-7.

* cited by examiner

MULTI-DENSITY ALL SUTURE ANCHOR

CROSS-REFERENCES TO RELATED APPLICATIONS

This application is a national stage application under 35 U.S.C. 371 based on international patent application PCT/US18/65375 filed on Dec. 13, 2018, which claims priority to U.S. Provisional Patent Application Ser. No. 62/598,201, filed on Dec. 13, 2017.

BACKGROUND OF THE INVENTION

1. Field of the Invention

The present disclosure is directed generally to an all-suture anchor and, more particularly, to an all-suture anchor composed of materials of varying densities.

2. Description of Related Art

Currently, all-suture anchors used to re-attach soft tissue to bone are generally composed of a single material having a uniform density. FIG. 1 shows an example of a conventional all-suture anchor 1. The all-suture anchor 1 includes a braid 2 composed of a single material with a passing suture 3 woven therethrough for deployment. This homogenous all-suture anchor structure is relatively smooth and soft in nature. As a result, current all-suture anchors rely on expansion that is controlled by the density of the bone in addition to the mechanics of the anchor when it is deployed.

Many conventional arthroscopic all-suture anchors are set or deployed by hand. These hand-set all-suture anchors pull out of hard and soft bone more readily than all-suture anchors deployed by a driver/inserter mechanism (although, some anchors deployed by a driver/inserter mechanism pull out after being set).

Therefore, there is a need for a suture anchor made of a material(s) that is optimal for generating bone compression and increased interference fixation post-installation.

SUMMARY OF THE INVENTION

The present invention is directed to an all-suture anchor composed of a material(s) with a density (or densities) that is optimal for generating bone compression and increasing interference fixation post-installation. According to one aspect, the all-suture anchor includes a fibrous construct which is movable between a pre-deployment configuration and a deployed configuration. The fibrous construct has a first density. The all-suture anchor also includes a monofilament woven through the fibrous construct. The monofilament has a second density, which is different than the first density.

According to another aspect, the present invention includes a method for deploying an all-suture anchor. The method includes the steps of: (i) providing an all-suture anchor having a fibrous construct movable between a pre-deployment configuration and a deployed configuration, the fibrous construct having a first density and a monofilament woven therethrough, the monofilament having a second density which is different than the first density; (ii) weaving a passing suture through the all-suture anchor; (iii) loading the all-suture anchor in a pre-deployment configuration onto a driver; and (iv) driving the all-suture anchor into a bone hole using the driver. The monofilament is preferably fixed with respect to the fibrous construct after it is woven through the fibrous construct, as opposed to a passing suture that can move through the fibrous construct (at least in the pre-deployment configuration).

Suture material or sutures, as the terms are used and described herein, can include monofilament or multi-filament suture as well as any other metallic or non-metallic filamentary or wire-like material suitable for performing the function of a suture. This material can include both bio absorbable and non-absorbable materials.

Suture anchors, as the term is used herein, can include soft suture anchors and rigid suture anchors. Soft suture anchors are formed from filaments of suture material which are retained within pre-formed bone holes by being deformable to increase their diameter to a size greater than that of the bone hole, to thereby reside within the cancellous bone and under the bone cortex. One such suture anchor is disclosed in U.S. Pat. No. 9,826,971 assigned to the assignee hereof and incorporated by reference herein in its entirety. Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) and a suture or filament portion. Methods and devices for inserting/deploying such all-suture anchors are known, examples of which are disclosed in U.S. Pat. No. 9,173,652.

As described in U.S. Pat. No. 8,409,252, for example, "non-soft," "hard" or "rigid" suture anchors generally include a "hard" anchor body portion (that may or may not include inner and outer members) and a suture/filament portion. The anchor body of such suture anchors may be formed of a biocompatible and/or bio absorbable material. These materials may be of such composition that they are reabsorbed by the body, e.g., during the healing process of the bone. Exemplary materials that are suitable for use in the inner and outer members include, but are not limited to, polyetheretherketone ("PEEK"), polylactic acid/beta-tricalcium phosphate ("PLA/Beta-TCP") composites, ultra-high molecular weight polyethylene ("UHMWPE"), as well as other metallic, non-metallic, and polymeric materials.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
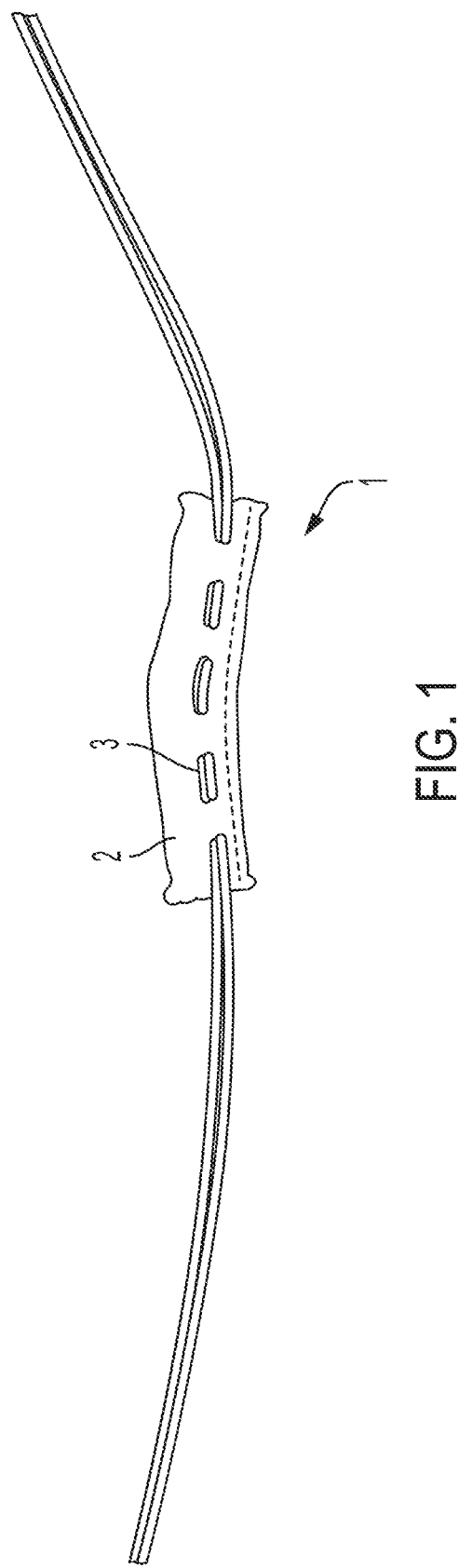
FIG. 1 is a top view of an all-suture anchor of the prior art.
Figure 2:
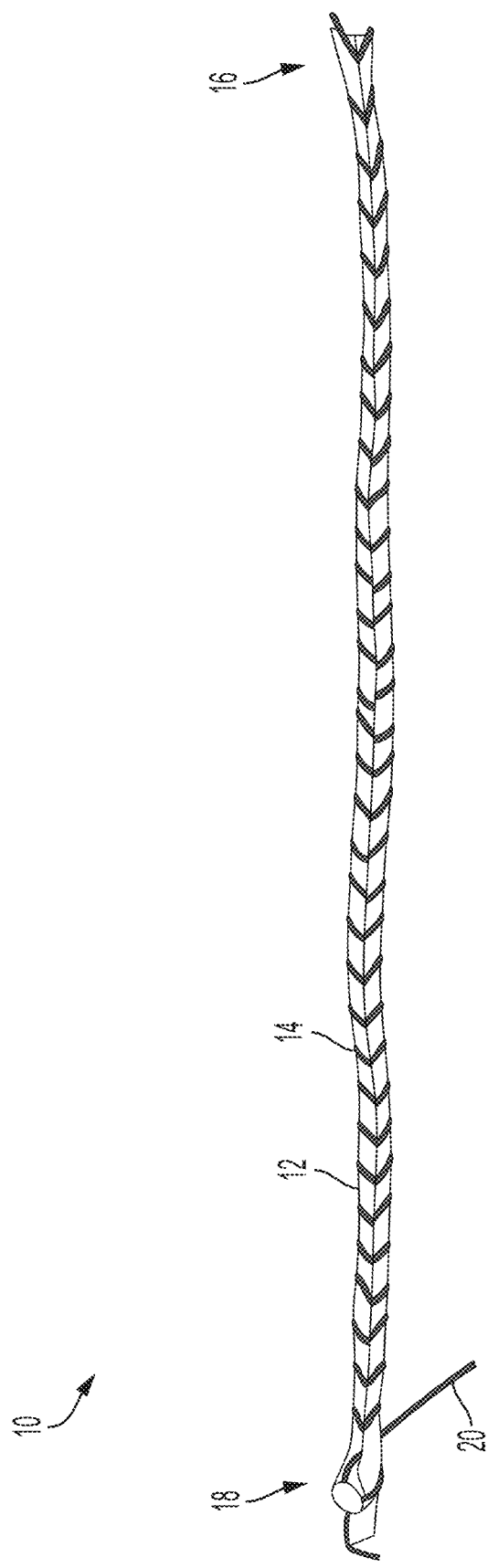
FIG. 2 is a top perspective view schematic representation of an all-suture anchor, according to an embodiment.

Referring now to the figures, wherein like reference numerals refer to like parts throughout, FIG. 2 shows a top perspective view schematic representation of an all-suture anchor 10, according to an embodiment. In the depicted embodiment, the all-suture anchor 10 comprises a fibrous construct 12 and a monofilament 14 woven therethrough. The fibrous construct 12 can be any fibrous, braided (e.g., uniform or non-uniform braid) or woven fabric-type structure having a first density.

Figure 7:
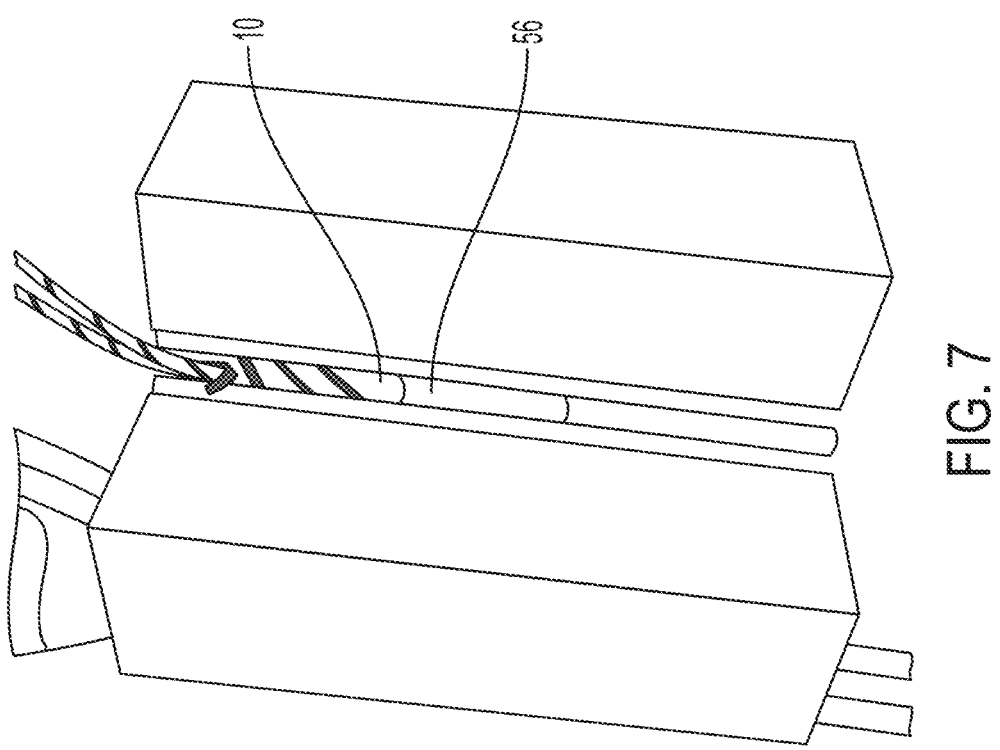
FIG. 7 is a side sectioned view schematic representation of an all-suture anchor deployed in a bone hole, according to an embodiment.

In the embodiment depicted in FIG. 2, the fibrous construct 12 is a flat length of suture having and extending between a first end 16 and a second end 18. In alternative embodiments, the fibrous construct 12 can also be a tube braid or cored suture (as should be understood by a person of ordinary skill i the art in conjunction with a review of this disclosure). The fibrous construct 12 is movable between a pre-deployment configuration, as shown in FIG. 2, and a deployed configuration, as shown in FIG. 7. The fibrous construct 12 may be composed of any traditional suture material, such as polyethylene (e.g., UHMWPE). The fibrous construct 12 can be, for example, 1.5-2.5 mm in width, 0.350-0.399 mm in depth, and at least 6 inches long. In an embodiment, the fibrous construct 12 has, for example, a width of 2 mm and a depth of 0.37 mm. The fibrous construct 12 can also have, for example, an average USP knot pull strength ≥30.00 LBF, with no individual value <26.00 LBF.

Still referring to FIG. 2, the monofilament 14 has a second density which is different (higher or lower) from the first density (i.e., density of the fibrous construct 12). In an embodiment, the monofilament 14 can be, for example, USP #2/0 suture and is at least 6 inches in length. The monofilament 14 can be composed of any traditional suture material, such as nylon, for example. The monofilament 14 can have, for example, an average USP knot pull strength ≥4.0 LBF, with no individual value <3.8 LBF. In alternative embodiments, the monofilament 14 may be segmented suture of multiple densities (e.g., suture with both a second density, a third density, a fourth density . . . ), or suture joined with a length of one or more sutures having contrasting (e.g., third, fourth . . . ) densities. The monofilament 14 is woven through the fibrous construct 12 from the first end 16 to the second end 18 (although, it does not have to stretch all the way to both ends, it can exist as it is woven through between both ends). As shown in FIG. 2, the monofilament 14 can be woven through the fibrous construct 12 using a needle 20.

Figure 3:
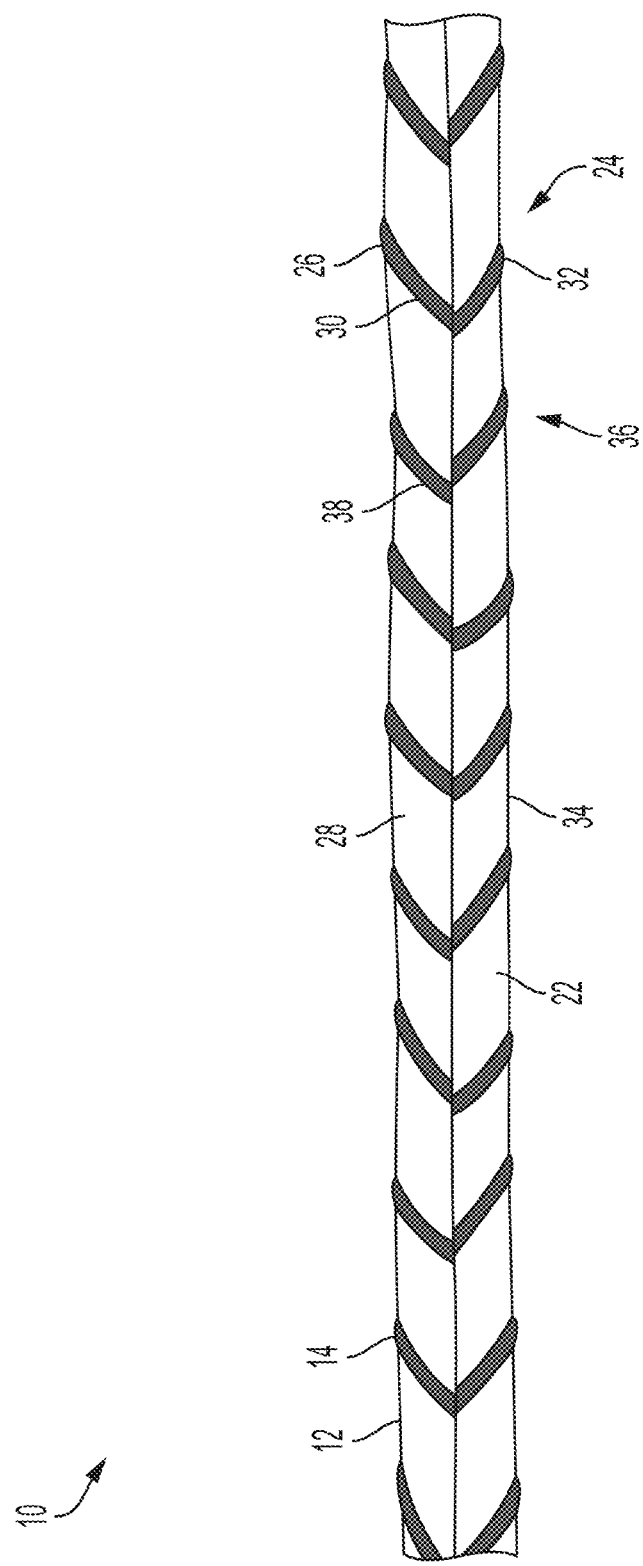
FIG. 3 is a close-up top view schematic representation of the all-suture anchor of FIG. 2.

In an embodiment, the monofilament 14 is threaded through the needle 20 and the needle 20 is used to pull the monofilament 14 through the fibrous construct 12 to create a "baseball" stitch, for example, as shown in FIG. 3. In an embodiment, the monofilament 14, for example, is woven through the fibrous construct 12 using a whip stitching technique to achieve the baseball stitch configuration. The fibrous construct 12 is tensioned and the monofilament 14, formed in a continuous loop, is threaded onto the needle 20. The loop of monofilament 14 is placed around the fibrous construct 12 such that the fibrous construct 12 is extending through the loop of monofilament 14.

Then, the needle 20 is used to puncture a first surface 22 of the fibrous construct 12 along a central longitudinal y-y axis extending through the fibrous construct 12 from the first end 16 to the second end 18. The needle 20 is pulled through the fibrous construct 12 to a second surface (not shown) and the monofilament 14 is pulled tight such that the monofilament 14 is snug on the first surface 22 of the fibrous construct 12. As a result, the first stitch 24 includes a first portion 26 of monofilament 14 extending from a first side 28 of the fibrous construct 12 to a first central passing location 30 (meaning a location near or along the central longitudinal y-y axis) and a second portion 32 of monofilament 14 extending from a second side 34 of the fibrous construct 12 to the first central passing location 30, as shown in FIG. 3.

After the first stitch 24 is placed, the loop of monofilament 14 extends from the bottom surface (not shown) of the fibrous construct 12. To place additional stitches 36, the loop of monofilament 14 is pulled back around the fibrous construct 12. Stated differently, the fibrous construct 12 is pulled or extended through the loop of monofilament 14 again. Thereafter, the needle 20 is passed through a subsequent second central passing location 38, spaced from the first central passing location 30. The monofilament 14 is pulled tight, securing a second stitch 36. The method is repeated to place as many stitches 36 as desired along the length of the fibrous construct 12 to create added texture or irregularities in the all-suture anchor 10. Preferably, there are 6-8 central passing locations along the length of the fibrous construct 12 and at least 6 inches of the fibrous construct 12 contains woven monofilament 14. In an embodiment, the first and second ends 16, 18 of the fibrous construct 12 are left unstitched with monofilament 14.

In accordance with other embodiments of the present invention, the stitch design does not have to look like what is shown in FIG. 3. Whatever the look of the monofilament 14 being weaved through the fibrous construct 12, it is preferable that a portion of the monofilament 14 extend from the outside surface of the fibrous construct 12 in order for an outside surface of the portion of the monofilament 14 to be able to grip to the surface of a bone hole upon deployment of the anchor. In addition, multiple monofilaments 14 of the same or different material with the same or different densities can be woven through a fibrous construct 12, for added bone surface grip capability benefit.

In alternative embodiments, the all-suture anchor 10 comprises additional features for creating irregularity within the bone surface when the all-suture anchor 10 is deployed. For example, the fibrous construct 12 may comprise rigid, mechanical barbs (or other similar protrusions, as should be understood by a person of ordinary skill in the art in conjunction with a review of this disclosure) on an exterior surface of the fibrous construct 12. In other examples, the monofilament 14 (or fibrous construct 12) may comprise added texture or rigidity along its length (which can, but does not have to be, composed of a material of yet another different density), which creates greater interference for fixation, as shown in FIGS. 5-6.

Figure 4:
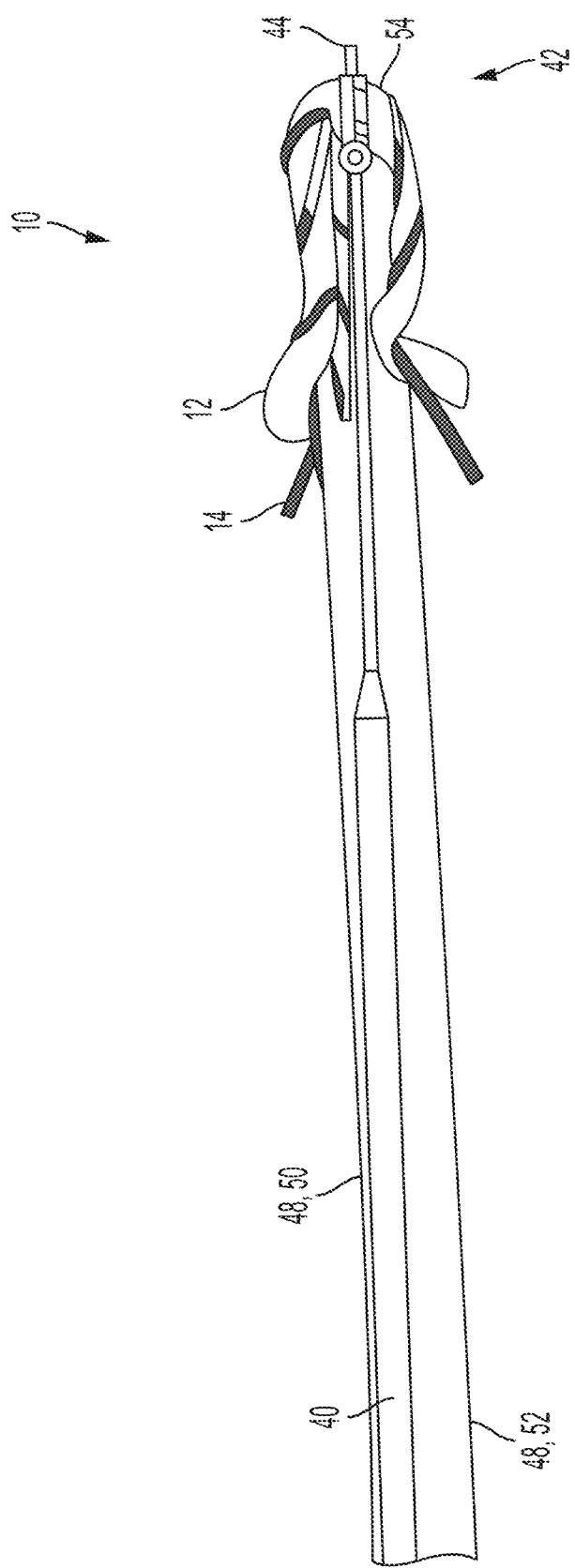
FIG. 4 is a side view schematic representation of an all-suture anchor loaded on a driver, according to an embodiment.
Figure 5:
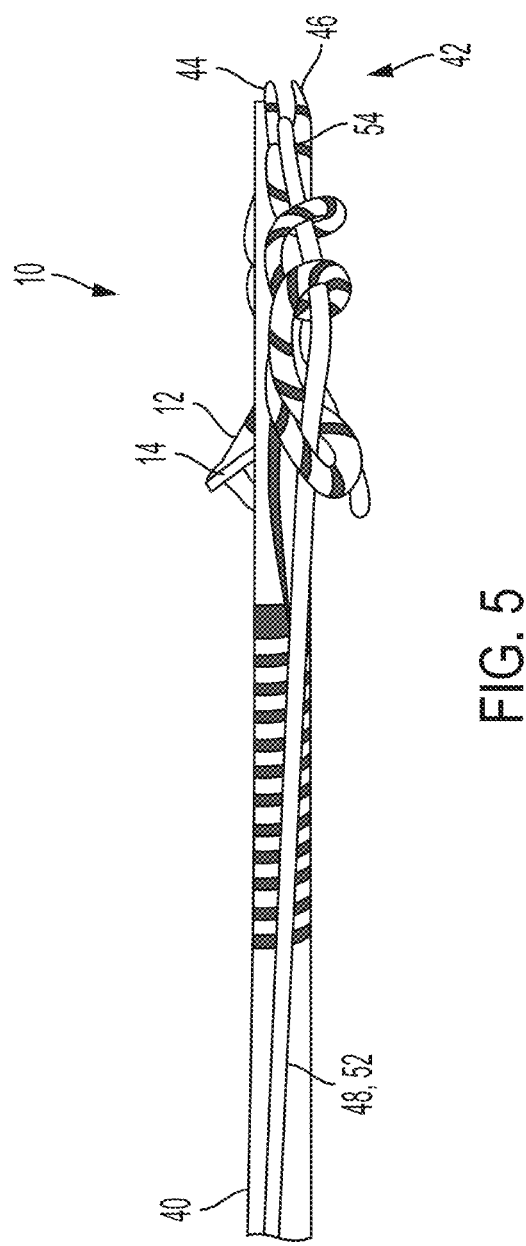
FIG. 5 is a side perspective view schematic representation of an all-suture anchor loaded on a driver, according to an alternative embodiment.
Figure 6:
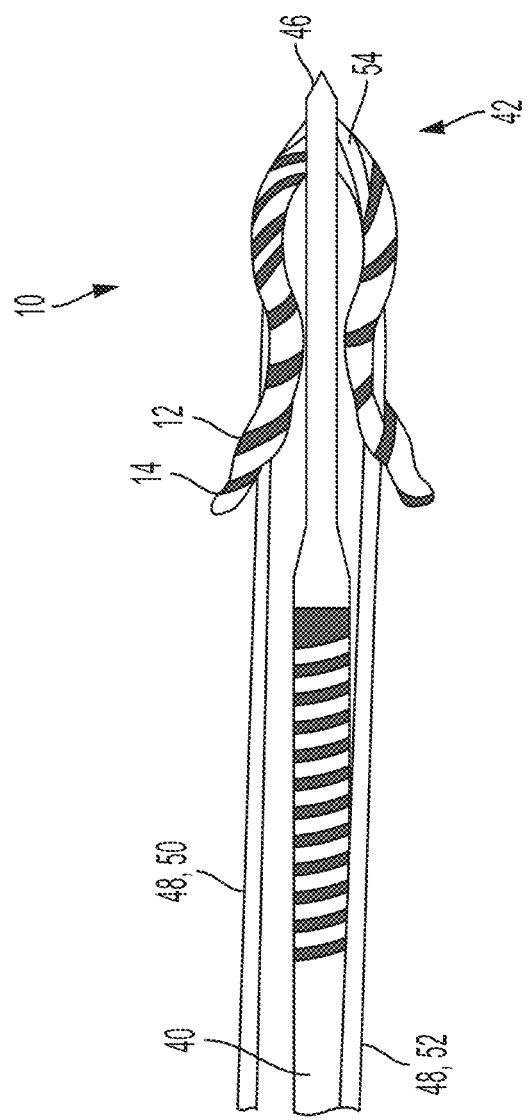
FIG. 6 is a side view schematic representation of the all-suture anchor of FIG. 5 loaded on a driver, according to an alternative embodiment.

Turning now to FIGS. 4-6, there are shown various views schematic representations of the all-suture anchor 10 loaded on a driver 40. The driver 40 shown in FIG. 4, for example, can be any standard anchor driver. In the depicted embodiment, the driver 40 has a pronged end 42 with spaced first and second arms 44, 46 (FIG. 5). To prepare the all-suture anchor 10 for deployment, a passing suture 48 is threaded through the all-suture anchor 10 in the pre-deployment configuration, as shown in FIGS. 4-6. A first end 50 of the passing suture 48 extends from the first end 16 of the all-suture anchor 10 and a second end 52 of the passing suture 48 extends from the second end 18 of the all-suture anchor 10.

With the passing suture 48 extending through the all-suture anchor, the all-suture anchor 10 can be loaded onto the driver 40. To load the all-suture anchor 10, the all-suture anchor 10 is placed between the first and second arms 44, 46 of the pronged end 42. The all-suture anchor 10 is placed in the pronged end 42 such that a portion of the fibrous construct 12 between the first and second ends 16, 18 is placed between the arms 44, 46, and the first and second ends 50, 52 of the passing suture 48 extend on opposing sides of the driver 40, as shown in FIGS. 4-6. In an embodiment, an approximately central portion 54 of the fibrous construct 12 is placed between the arms 44, 46.

Referring now to FIG. 7, there is shown a side sectioned view schematic representation of an all-suture anchor 10 deployed in a bone hole 56, according to an embodiment. With the all-suture anchor 10 in the pre-deployment configuration loaded on the driver 40, as shown in FIGS. 4-6, the pronged end 42 of the driver 40 is pushed into the bone hole 56. When the all-suture anchor 10 is within the bone hole 56, the driver 40 can be removed. The passing suture 48 is tensioned to deploy the all-suture anchor 10. The contrasting density (i.e., irregularities) of the fibrous construct 12 and the monofilament 14 woven therethrough generates bone compression and additional interference fixation. As a result, the all-suture anchor 10 has additional purchase in hard and soft bone as compared to all-suture anchors composed of a single material (or multiple materials) of one density. For example, the all-suture anchor 10 has more power in hard bone, such as in a hip, as compared to conventional all-suture anchors (of uniform density). With the all-suture anchor 10 in place, the passing suture 48 can be used to secure a soft tissue in a desired position relative to the bone hole 56. In addition, the all suture anchor 10 can be deployed such that the thickness of the fibrous construct 12 is greater in the deployed state as compared to the thickness of the fibrous construct 12 in an un-deployed state.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. An all-suture anchor, comprising:
   a fibrous construct having a central longitudinal axis extending from a first end of the fibrous construct to a second end of the fibrous construct and movable between a pre-deployment configuration and a deployed configuration, the fibrous construct having a first density;
   a monofilament woven through the fibrous construct along the central longitudinal axis to form at least one stitch, the monofilament having a second density, which is different than the first density,
   wherein the stitch comprises a first portion extending from a first side of the fibrous construct to a first passing location and a second portion extending from a second side of the fibrous construct to the first passing location wherein the monofilament passes through the fibrous construct in at least the first passing location and a second passing location and extends around the first side of the fibrous construct between the first passing location and the second passing location and the second portion of the monofilament extends around the second side of the fibrous construct between the first passing location and the second passing location.

2. The all-suture anchor of claim 1, further comprising a driver, wherein the fibrous construct is loaded on the driver.

3. The all-suture anchor of claim 2, wherein the driver comprises a pronged end having a first arm and a second arm, and the fibrous construct is between the first arm and the second arm.

4. The all-suture anchor of claim 1, further comprising one or more barbs on an exterior surface of the fibrous construct.

5. The all-suture anchor of claim 1, wherein the fibrous construct is a flat suture braid.

6. The all-suture anchor of claim 1, wherein the fibrous construct is composed of ultra-high molecular weight polyethylene ("UHMWPE").

7. The all-suture anchor of claim 1, wherein the monofilament comprises a segment of a third density.

8. The all-suture anchor of claim 1, further comprising a second monofilament woven through the fibrous construct, the second monofilament having a third density, which is different than the first density.

* * * * *